(12) United States Patent
Roesch et al.

(10) Patent No.: US 9,540,984 B2
(45) Date of Patent: Jan. 10, 2017

(54) METHOD FOR CONDITION DETERMINATION OF AN EXHAUST-GAS PURIFICATION SYSTEM

(75) Inventors: Martin Roesch, Rodgau (DE); Martin Votsmeier, Luetzelsachsen Stadt Weinheim (DE); Ralf Moos, Bayreuth (DE); Gerhard Fischerauer, Bayreuth (DE); Gunter Hagen, Helmsbrechts (DE); Sebastian Reiss, Bayreuth (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 222 days.

(21) Appl. No.: 14/232,790

(22) PCT Filed: Jul. 12, 2012

(86) PCT No.: PCT/EP2012/063645
§ 371 (c)(1),
(2), (4) Date: Apr. 16, 2014

(87) PCT Pub. No.: WO2013/010897
PCT Pub. Date: Jan. 24, 2013

(65) Prior Publication Data
US 2014/0283503 A1    Sep. 25, 2014

(30) Foreign Application Priority Data
Jul. 15, 2011   (DE) .................. 10 2011 107 784

(51) Int. Cl.
*G01M 15/10* (2006.01)
*F01N 11/00* (2006.01)
(Continued)

(52) U.S. Cl.
CPC ............. *F01N 11/002* (2013.01); *F01N 11/00* (2013.01); *G01N 22/00* (2013.01); *F01N 3/0842* (2013.01);
(Continued)

(58) Field of Classification Search
CPC ....... F01N 11/00; F01N 2550/02; G01M 15/10
(Continued)

(56) References Cited

U.S. PATENT DOCUMENTS 4,580,441 A * 4/1986 Sakurai et al. ............. 73/23.33
5,423,180 A * 6/1995 Nobue et al. .................. 60/274
(Continued)

FOREIGN PATENT DOCUMENTS

| DE | 101 03 772 A1 | 9/2002 |
|----|---------------|--------|
| DE | 103 58 495 A1 | 7/2005 |
| DE | 10 2008 012050 A1 | 9/2009 |

OTHER PUBLICATIONS

International Search Report for PCT/EP2012/063645, Mailed Sep. 9, 2012.
(Continued)

*Primary Examiner* — Eric S McCall
(74) *Attorney, Agent, or Firm* — Smith, Gambrell & Russell, LLP

(57) ABSTRACT

The present invention relates to a process for determining the state of an exhaust-gas purification device. The exhaust-gas purification device is one which can store gas and/or particles. By means of the proposed process, it is for example possible for the loading state of the exhaust-gas aftertreatment system, for example the oxygen storage state of a catalytic converter which is provided with an oxygen-storing material, such as for example a three-way catalytic converter, to be analyzed. The present process operates contactlessly through the analysis of resonances which arise upon the excitation of the catalytic converter using the purification device as microwave cavity resonator.

14 Claims, 4 Drawing Sheets

(51) Int. Cl.
*G01N 22/00* (2006.01)
*F01N 3/08* (2006.01)
*F01N 3/10* (2006.01)
*F01N 3/20* (2006.01)

(52) U.S. Cl.
CPC .............. *F01N 3/101* (2013.01); *F01N 3/2066* (2013.01); *F01N 2550/02* (2013.01); *F01N 2550/03* (2013.01); *F01N 2560/12* (2013.01); *F01N 2900/1622* (2013.01); *F01N 2900/1624* (2013.01); *Y02T 10/22* (2013.01); *Y02T 10/47* (2013.01)

(58) Field of Classification Search
USPC ...................................................... 73/114.75
See application file for complete search history.

(56) References Cited

U.S. PATENT DOCUMENTS

| | | |
|---|---|---|
| 6,655,129 B2 | 12/2003 | Lindner et al. |
| 2007/0022746 A1* | 2/2007 | Decou ..................... F01N 9/002 60/295 |
| 2007/0101705 A1* | 5/2007 | Knitt ....................... F01N 3/021 60/295 |
| 2008/0018442 A1* | 1/2008 | Knitt ....................... F01N 3/025 340/438 |
| 2009/0229581 A1* | 9/2009 | Ikeda ............................ 123/536 |
| 2010/0186384 A1* | 7/2010 | Gonze ..................... F01N 3/023 60/286 |
| 2010/0212299 A1 | 8/2010 | George et al. |
| 2014/0331752 A1* | 11/2014 | Hall ......................... F01N 11/00 73/114.75 |
| 2016/0032850 A1* | 2/2016 | Sunley ................ F02D 41/0245 60/274 |

OTHER PUBLICATIONS

Ralf Moos, et al., "Direct Catalyst Monitoring by Electrical Means: An Overview on Promising Novel Principles", Topics in Catalysis, 52 (2009), 2035-2040.

Fischerauer, et al., "Sensing the soot load in automotive diesel particulate filters by microwave methods", Measurement Science and Technology, vol. 21, Mar. 1, 2010, art. Number 35108. pp. 1-6.

* cited by examiner

METHOD FOR CONDITION DETERMINATION OF AN EXHAUST-GAS PURIFICATION SYSTEM

FIELD OF THE INVENTION

The present invention relates to a process for determining the state of an exhaust-gas purification device. The exhaust-gas purification device is one which can store gas and/or particles. By means of the proposed process, it is for example possible for the loading state of the exhaust-gas aftertreatment system, for example the oxygen storage state of a catalytic converter which is provided with an oxygen-storing material, such as for example a three-way catalytic converter, to be analysed. The present process operates contactlessly through the analysis of resonances which arise upon the excitation of the catalytic converter with high-frequency electromagnetic waves.

BACKGROUND OF THE INVENTION

Ever more stringent exhaust-gas laws together with the pressure to reduce fuel consumption necessitate new concepts both for the internal combustion engine and also for exhaust-gas purification. This also demands new concepts for the control and monitoring of exhaust-gas purification systems.

For example, in the case of the stoichiometrically operated applied-ignition engine (so-called "λ=1 engine"), the air/fuel ratio λ (also referred to as the air number) of the untreated exhaust gas is detected by means of a first λ probe. In the event of a control deviation from the setpoint value λ=1, the air/fuel ratio is then corrected. It is necessary for approximately λ=1 to be adhered to on average over time. Owing to the oxygen storage capacity of the so-called "three-way catalytic converter" arranged downstream of the first λ probe, optimum conversion takes place for as long as the catalytic converter is still in a good state. With decreasing catalytic converter quality, which is manifested in a reduction of the conversion rate and a rise in the light-off temperature, the capability of the catalytic converter to store oxygen also decreases. A second λ probe arranged downstream of the catalytic converter can detect this. For such an indirect process, in which the state of the oxygen-storing catalytic converter is inferred from the signals of the two λ probes, highly complex modelling is necessary, which necessitates in particular an engine operating state model, see for example J. Riegel et al., "Exhaust gas sensors for automotive emission control", Solid State Ionics 152-153 (2002), 783-800.

This is addressed by processes which determine the operating state and the quality of a catalytic converter which stores gases such as for example oxygen. In particular, it is possible with said processes to determine the extent to which the oxygen store of the catalytic converter is filled or where the oxygen loading front in the catalytic converter is situated, as shown for example in R. Moos, M. Wedemann, M. Spörl, S. Reiß, G. Fischerauer, "Direct Catalyst Monitoring by Electrical Means: An Overview on Promising Novel Principles", Topics in Catalysis, 52 (2009), 2035-2040. Of particularly simple design here are so-called high-frequency-based systems such as are described for example in DE102008012050 or in DE10358495.

In said processes, an electromagnetic microwave resonance is excited in the interior space of the catalytic converter housing formed as a cavity resonator, and the shift of the resonance frequency and/or quality is observed. The change in the resonance frequency is taken for example as a measure for the oxygen loading of the storage material of the catalytic converter. DE102008012050 proposes regulation based on this. When a predefinable value of the resonance frequency is attained, a regeneration is carried out. As already indicated in DE102008012050 and also presented therein for example on the basis of FIG. 8, the temperature of the system plays a significant role because the temperature causes a shift of the resonance frequencies. Even with knowledge of the catalytic converter temperature, however, it is not possible by means of the measurement system to directly derive important variables such as for example the oxygen loading. The background to this is that firstly the resonance frequencies are dependent on the geometry, and secondly the temperature dependency of the loading is unknown. Specifically the geometry aspect also prevents a high-frequency-based measurement system installed in the exhaust tract from being able to be used without further calibration, because the component variance with regard to geometric dimensions and with regard to a layer thickness variance of the coating and with regard to the reproducibility of the electrical properties of the ceramic substrate (of the honeycomb body) can lead to variance in the resonance frequencies, which variance is of the order of magnitude of the measurement effect.

BRIEF SUMMARY OF THE INVENTION

It is the problem of the present invention to eliminate the stated disadvantages of the methods of the prior art. In particular, the process according to the invention should be capable, through a type of calibration, of for example minimizing the abovementioned external influences on the resonance signal.

This problem, and other problems which emerge in an obvious manner from the prior art, are solved by means of a method having features set forth in the present disclosure.

The present disclosure also sets forth a number of preferred embodiments of the method according to the invention.

By virtue of the fact that, in a process for calibrating a measurement device for determining the electrical properties of a component for exhaust-gas aftertreatment, which component accumulates or stores exhaust-gas constituents and is arranged in a metallic housing of an exhaust-gas aftertreatment system of a vehicle, wherein the electrical properties are detected by means of microwaves which are coupled in and/or coupled out by means of at least one antenna arranged in the housing at the inflow side and/or at the outflow side, a measurement at low temperature of the component for exhaust-gas aftertreatment serves as a basis for the calibration of the measurement device, and a correction of the measurement device takes place on the basis thereof, wherein low temperatures are characterized in that a distinction can no longer be made between different loading or storage states of the component, one arrives in an extremely simple but no less advantageous manner at the solution to the stated problem. By means of the process described here, it is possible for a gas- and/or particle-storing exhaust-gas purification device (2) to be inspected contactlessly with regard to its present electrical properties, in particular electrical conductivity, in order thereby for example to be able to infer its present storage state.

The determination of the electrical properties and the calibration of the measurement device may be carried out not only through the use of the resonance frequency but rather also by means of further signal features such as amplitude, the quality of the resonator or else variables based thereon (also in different frequency ranges).

The calibration process of the high-frequency measurement device may be used in particular for three-way catalytic converters for the detection of the oxygen loading but also for further catalytic converter types such as $NO_x$ storage catalytic converters ($NO_x$ loading), SCR catalytic converters ($NH_3$ loading) and diesel particle filters (soot loading) which store gases or soot particles if, at a sufficiently low temperature, a distinction can no longer be made between the laden and unladen state. The unladen state can also be induced deliberately in this case.

By means of suitable extrapolation, the temperature dependency of a base measurement can be taken as a basis, whereby the electrically insulating state is known and can be updated over the service life on the basis of the calibration measurement.

By means of a suitable mathematical relationship, the difference between the laden and unladen state can be calculated and thus also taken into consideration in the on-board diagnosis as a measurement variable for the overall storage capacity of the component of the exhaust-gas aftertreatment device in relation to the new state.

The component and the antennae may be surrounded at the inflow side and at the outflow side by a microwave reflector for delimiting the resonator volume.

It is a special characteristic of the present process that the proposed process can be used not only for calibration and application but rather also within the regulation of engines.

DETAILED DESCRIPTION OF THE INVENTION

Figure 1:
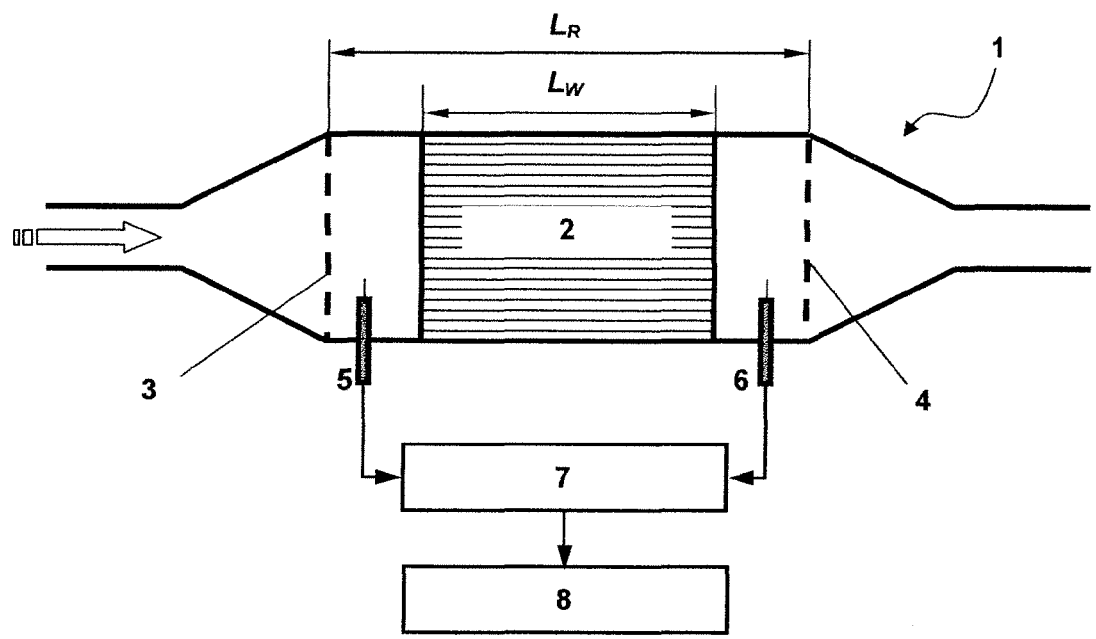
FIG. 1 shows the basic design of an exhaust-gas aftertreatment system having a housing part (1) into which are installed a three-way catalytic converter (2), a measurement system having two antennae (5, 6), one of which is optional, activation (7) and evaluation electronics (8) and an optional temperature sensor (see DE102008012050) and optional reflector (3, 4)

The present process is particularly advantageously suitable for determining the state of a gas- and/or particle-storing exhaust-gas purification device (2) which is arranged in a metallic housing (1) of an exhaust-gas aftertreatment system of a vehicle, the state of which exhaust-gas purification device is detected, by means of microwaves which are coupled in and/or coupled out by means of at least one antenna (5, 6) arranged in the housing at the inflow side and/or at the outflow side, in that:

a) as a base measurement, the temperature dependency of a resonance characteristic of the system below a threshold temperature is determined;

b) in operating situations of the vehicle in which the exhaust system lies below the threshold temperature, a resonance characteristic is measured;

c) the difference between the measurement of the value from b) and the corresponding base measurement in a) is determined; and d) from the resonance characteristic determined in certain driving situations in which the exhaust system is above the threshold temperature, incorporating the difference from c), the state of the exhaust-gas purification device (2) is analysed. By means of the embodiment of the invention described here, it is possible for a gas- and/or particle-storing exhaust-gas purification device (2) to be inspected contactlessly with regard to its present electrical conductivity, in order thereby to be able to infer for example its present storage state or possible damage. The system is thus firstly calibrated against the base measurement before the electrical properties of the component are inferred from the then determined and corrected value for the resonance characteristic.

The essential aspect of the present method is the fact that, below a threshold temperature $T_G$, the resonance characteristics of the system are evidently independent of the state of the gas- and/or particle-storing exhaust-gas purification device (2) (see FIG. 4). This fact makes it possible for the reference characteristics below said threshold temperature to be taken into consideration as a calibration benchmark. The present fill level or capacity of the gas- and/or particle-storing exhaust-gas purification device (2) is normally not known. Therefore, the calibration of the system on the basis of said described independence of the resonance characteristic below the threshold temperature can be carried out in a simple manner. It is only above the threshold temperature that the resonance characteristics differ as a function of the temperature and for example the loading (see FIG. 4). The threshold temperature is thus characterized in that, below said temperature, corresponding resonance characteristics lie approximately on one curve regardless of the fill level of the gas- and/or particle-storing exhaust-gas purification device (2), and thus no longer differ.

Accordingly, it is provided according to the invention that, in a first step, a base measurement is carried out, wherein special resonance characteristics at least below the threshold temperature are measured. The base measurement should take place as early as possible after the assembly of the exhaust-gas purification system. Here, the gas- and/or particle-storing exhaust-gas purification device (2) has often not yet experienced any aging, damage or other influences. When the vehicle with the gas- and/or particle-storing exhaust-gas purification device (2) is then in normal operation, a resonance characteristic is measured regularly in operating states in which the exhaust system and therefore also the gas- and/or particle-storing exhaust-gas purification device (2) are below the threshold temperature. From the comparison with the corresponding base measurement, it is now possible if appropriate to detect a difference arising from aging, damage or other influences but not from the degree of loading. Correspondingly utilizable operating states arise whenever the temperature of the exhaust system is low. This is the case for example upon start-up or during long idle periods of the vehicle. The difference discussed above is then taken into consideration as a corrective value for every further measurement during normal driving operation, when the exhaust system is often above the threshold temperature. Only on the basis of the thus determined and correspondingly corrected value is the further analysis of the gas- and/or particle-storing exhaust-gas purification device (2) then carried out.

A person skilled in the art is familiar with which states should advantageously be inspected for the exhaust-gas purification devices being considered here. First of all, the expression "state of the exhaust-gas purification device (2)" is to be understood to mean a variable selected from the group comprising loading state, storage capacity and aging state. It is very particularly preferable for the present loading state or the present storage capacity of the exhaust-gas purification device (2) to be inspected. The loading state is important because it allows conclusions to be drawn regarding when the exhaust-gas purification device must possibly be regenerated, or for example how the air/fuel ratio of the exhaust gas should be adapted to be able to attain a certain fill level of the storage material. For example, it is known that a three-way catalytic converter functions particularly well when its oxygen store is neither completely full nor completely discharged. Said three-way catalytic converter is then capable of compensating relatively small fluctuations in the air/fuel ratio and thus providing a constantly expedient $\lambda$ value of approximately 1. With regard to the storage capacity, it is noted that in particular gas-storing materials in the exhaust-gas purification device (2) are subject to aging inter alia owing to the high temperatures which prevail at times. Said aging process is characterized in that the material in the aged state is less capable of filtering corresponding gas components out of the exhaust gas of the vehicle. Consequently, it must be noted that the storage capacity of a device of said type decreases with progressive running time of the vehicle, for example as a result of aging or other damage, which is manifested in changed curve profiles for the temperature dependency of the fully laden and definedly discharged exhaust-gas purification device (2), compared with the base measurement. It is therefore important for the correct functioning of the exhaust-gas purification device (2) that the storage capacity of the gas-storing material be continuously monitored. In the case of too low a storage capacity, the corresponding exhaust-gas purification device can then be changed during the course of a service.

In particular the abovementioned state variables of the exhaust-gas purification system (2) are dependent on the present driving situation of the vehicle and in particular on the temperature of the exhaust system. To obtain a meaningful assessment of the state variables, it is therefore necessary to correct the presently measured resonance characteristic in accordance with the invention. During driving operation, the exhaust-gas purification system (2) is often operated above the threshold temperature. A comparison of the presently measured value of the resonance characteristic with a corresponding value below the threshold temperature is not possible because the resonance characteristics of the system are subject to at least a certain system-dependent temperature dependency (see FIG. 4). Accordingly, it is advantageous for the presently measured value of the resonance characteristic to be compared with a value for the resonance characteristic which was determined or measured at the same temperature (as in FIG. 4). A person skilled in the art is now familiar with various possibilities as regards how he can attain such values above the threshold temperature mentioned in the introduction. It is possible, for example, for the reference characteristics, measured in the fresh state (as in the case of the base measurement), for a definedly laden or definedly discharged gas- and/or particle-storing exhaust-gas purification device (2) to be taken into consideration as reference values. In such a case, one obtains curves such as are illustrated by way of example in FIG. 4 for the oxygen-storing material in a three-way catalytic converter. The curves illustrated here, which were determined, as described above, in the fresh state (possibly after the assembly of the exhaust system in a new vehicle), may be stored in the ECU and thus taken into consideration as comparative values. It is however also possible for said curves to be determined in some other way. In this regard, a person skilled in the art is familiar with measures by which he can estimate or mathematically determine said values, in particular on the basis of the base measurement. The difference between the laden and unladen state can be calculated by means of a suitable mathematical relationship. Said difference can thus also be taken into consideration in the on-board diagnosis as a measurement variable for the overall storage capacity of the component of the exhaust-gas aftertreatment device in relation to the new state.

According to the invention, resonance characteristics determined in the present process are compared with one another. It is self-evident that the comparisons are carried out only between like, and thus corresponding, resonance characteristics. As such, a person skilled in the art will give consideration in particular to variables selected from the group comprising resonance frequency, amplitude, the magnitude of the reflection parameter $S_{11}(f_{res})$, the magnitude of the transmission factor or the width of the resonance peak or of the resonance trough or other variables derived from the S parameters (in this regard, see DE102008012050). Particularly preferable in this context is the resonance frequency or magnitude of the reflection parameter $S_{11}$ or $S_{12}$. Very particularly preferable in this context is the evaluation by means of the resonance frequency (see FIGS. 2 and 3).

As already indicated further above, the present process is based on the fact that the resonance characteristics change for example with progressive aging and/or the loading state of the exhaust-gas purification system (2). For example, the increasing loading evidently results in the conductivity or the dielectric constant of the material of the exhaust-gas purification system (2) being modified. As a result, with increasing loading, it is for example the case that the resonance frequencies shift toward higher frequencies. The exhaust-gas purification system (2) being considered here encompasses primarily gas- and/or particle-storing devices. As such, all devices which a person skilled in the art would take into consideration for this purpose can be checked in accordance with the invention. Devices are preferable which are selected from the group comprising three-way catalytic converter provided with an oxygen storage material, if appropriate catalytically coated diesel particle filter, NOx storage catalytic converter, SCR catalytic converter with NH$_3$ storage function. Particularly preferable in this connection is the three-way catalytic converter provided with an oxygen storage material.

As already indicated in the introduction, there is a threshold temperature $T_G$ below which the curves for the reference characteristics converge on one curve. Accordingly, a threshold temperature $T_G$ is advantageously defined such that, below said temperature, the corresponding reference characteristics in the (arbitrarily) laden and (arbitrarily) unladen state of the gas- and/or particle-storing exhaust-gas purification device (2) differ by less than 10%. The corresponding reference characteristics particularly preferably differ by less than 5%, very particularly preferably by less than 3%.

In a preferred embodiment of the present invention, the three-way catalytic converter (2) and the antenna(e) (5, 6) at the inflow and outflow side are surrounded by a microwave reflector. Suitable for this purpose are all materials which oppose the exhaust-gas flow with the lowest possible counterpressure, but which are capable of reflecting the microwaves which are used. A person skilled in the art knows which devices can be taken into consideration here. In case of doubt, simple metallic grates may be of assistance.

The invention will be described in more detail on the basis of the following exemplary and non-restrictive explanations. Three-way catalytic converters with corresponding storage capabilities are well known to a person skilled in the art (see for example J. Kašpar et al., Automotive catalytic converters: current status and some perspectives, Catalysis Today 77 (2003) 419-449). Said catalytic converters are generally positioned in a metallic housing, which conducts the electrical current, in the exhaust tract. It is pointed out that the three-way catalytic converter need not imperatively be mounted in a metallic housing, as long as it is ensured that said three-way catalytic converter is accommodated in a device which serves as a resonance body for the high-frequency electromagnetic radiation (microwave range) envisaged here.

The antennae may be selected as specified by a person skilled in the art. Such equipment, and also the signal detection unit and the corresponding analysis unit, are well known to a person skilled in the art (for example from P. S. Neelakanta, Handbook of Electromagnetic Materials. CRC Press, Boca Raton etc., 1995 and from S. H. Chao, Measurements of microwave conductivity and dielectric constant by the cavity perturbation method and their errors, IEEE Transactions on Microwave Theory and Techniques 33 (1985) 519-526, or from the literature cited therein).

The present loading values of the oxygen storage material which are inter alia to be measured by means of the present process are important for the engine control, but it has been found that targeted filling of the storage material with oxygen up to a defined fraction of the storage capacity is preferable for the stoichiometric operation of a motor vehicle with applied-ignition engine (DE10103772). A person skilled in the art knows here, too, how he can correspondingly implement the engine control by means of an ECU. In this regard, reference is made also to DE102008012050.

The calibration can basically be carried out with any signal feature of the high-frequency measurement. As can be seen from FIGS. 2 and 3 and as indicated further above, there is for example a plurality of resonance frequencies expedient for the analysis of the three-way catalytic converter (2). The selection of the best resonance frequency is always significantly dependent on the ambient conditions, and should be determined in each individual situation. It is advantageously possible in the present case, for the determination of the resonance frequencies, to take into consideration a minimum of the magnitude of the reflection factor $S_{11}$ of the resonator between 1200 and 1300 MHz.

The frequency-dependent scattering matrix S, which also includes the reflection parameter $S_{11}(f)$, links the complex wave amplitudes $a_i$ (in Watt$^{1/2}$) of the waves entering the two gates with those of the exiting waves, $b_j$:

$$\begin{pmatrix} b_1 \\ b_2 \end{pmatrix} = S(f) \cdot \begin{pmatrix} a_1 \\ a_2 \end{pmatrix} = \begin{pmatrix} S_{11}(f) & S_{12}(f) \\ S_{21}(f) & S_{22}(f) \end{pmatrix} \cdot \begin{pmatrix} a_1 \\ a_2 \end{pmatrix}$$

At the resonance frequencies of the cavity resonator, the transmission factor magnitudes $|S_{12}|$ and $|S_{21}|$ have local maxima, whereas the reflection factor magnitudes $|S_{11}|$ and $|S_{22}|$ have local minima.

This is however illustrated here by way of example on the basis of the resonance frequency $f_{res}$. The resonance frequency $f_{res,measured}(T_0)$ is a resonance frequency measured on the present three-way catalytic converter. It is important here that said frequency is measured below a certain temperature ($T_0 < T_G$). As is clear from FIG. 4, it is only above a certain temperature, which differs between individual situations, that the resonance frequencies for the definedly oxygen-laden catalytic converter and the definedly discharged catalytic converter diverge (threshold temperature). According to the invention, said temperature is reached when the resonance frequencies in the definedly laden and definedly discharged three-way catalytic converter differ as described further above.

Said resonance frequency is subsequently compared with the resonance frequency $f_{res,lean}(T_0)$ from FIG. 4 (corresponds to the base measurement of the gas- and/or particle-storing exhaust-gas purification device (2)) and the difference is determined. Said difference is then taken into consideration as an aid for establishing new curves for the present three-way catalytic converter in the present environment, by virtue of the curves being formed by extrapolation from the curves of the base measurement (FIG. 4) on the basis of the determined difference. One thus arrives at a resonance frequency curve for the definedly laden ($f_{res,full}(T)$) catalytic converter (2) and the definedly discharged ($f_{res,empty}(T)$) catalytic converter (2).

If the presently measured actual values of the resonance frequency for the three-way catalytic converter (2) are now measured during operation of the vehicle, possible damage to or aging of the catalytic converter can be inferred from the deviations of the new curves with the actual values if the setpoint values which exist at a certain temperature are generally no longer attained for the definedly laden state and the definedly discharged state.

An exhaust-gas aftertreatment and measurement system such as is of interest for the present invention is illustrated in FIG. 1. The metallic housing of the catalytic converter acts as a (filled) cavity resonator which in this case can, by way of example, be operated as a single-gate resonator (only one antenna active). Here, the honeycomb body of length $L_W$ is inserted into the resonator of length $L_R$. The antennae are situated in each case between the honeycomb body and the (optional) shielding grates. For frequency-independent and connection pipe-independent, reproducible specification of the resonance volume, it may be advantageous (although not imperatively necessary for the method; see DE102008012050 FIG. 4a and FIG. 4b) for reflectors, for example metallic grates, to be provided on the ends of the catalytic converter housing, which reflectors do not inadmissibly hinder the exhaust-gas flow but act as electrical short-circuits for electromagnetic waves in the frequency range up to a few GHz. The antennae should be designed to be capable of withstanding high temperatures. Arrangements are for example suitable which have a metallic hollow cylinder as an outer conductor and, coaxial with respect thereto, a metallic inner conductor which is mounted via ceramic discs as spacers and which is longer than the outer conductor such that it protrudes into the resonance chamber (capacitive coupling). Likewise, a metal- or wire-filled insulating ceramic pipe, the filling of which is longer than the pipe, together with the conductive wall of the catalytic converter housing, or a small conductor loop, the end of which is connected in conducting fashion to the catalytic converter housing (magnetic coupling), may serve as an antenna. To detect changes in the honeycomb body, use may be made, as measurement signals, inter alia of amplitude, resonance frequency, half width or quality.

For the test described here, in principle only one antenna is required. From the externally measured S parameter $S_{11}$, which is in principle of complex value, of the cavity resonator (see above), features are extracted continuously as described above, said features having a clear relationship with the state of interest of the catalytic converter. A highly suitable feature is the resonance frequency, that is to say for example the frequency of the local minimum of the magnitude of $S_{11}$ in FIG. 2 or FIG. 3. As already mentioned above, the measurement and calibration process may also be carried out with other measurement variables of the high-frequency measurement.

Figure 2:
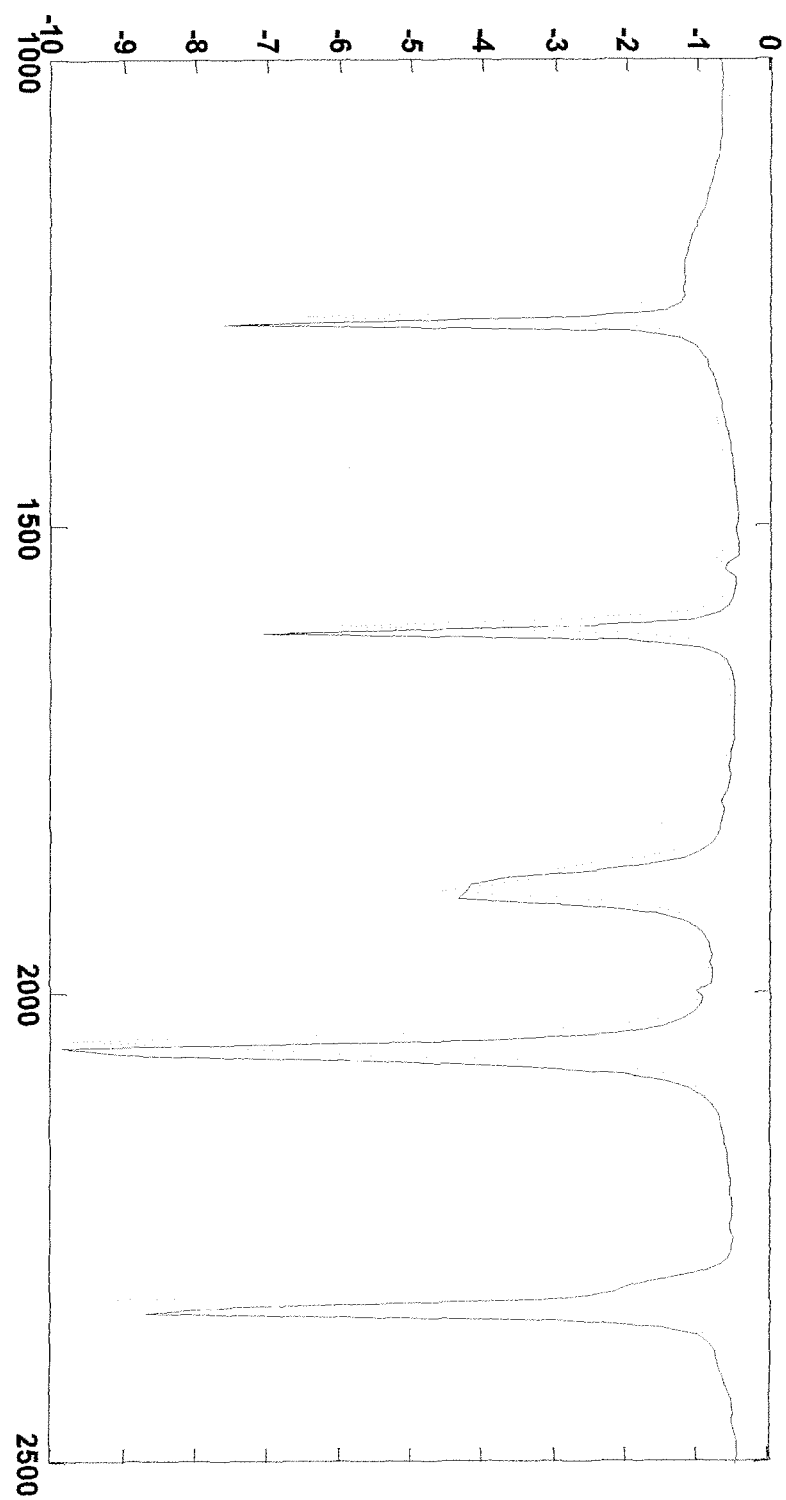
FIG. 2 shows the value of the reflection factor $S_{11}$ of the resonator at different temperatures in the fully oxygen-laden state.
Figure 3:
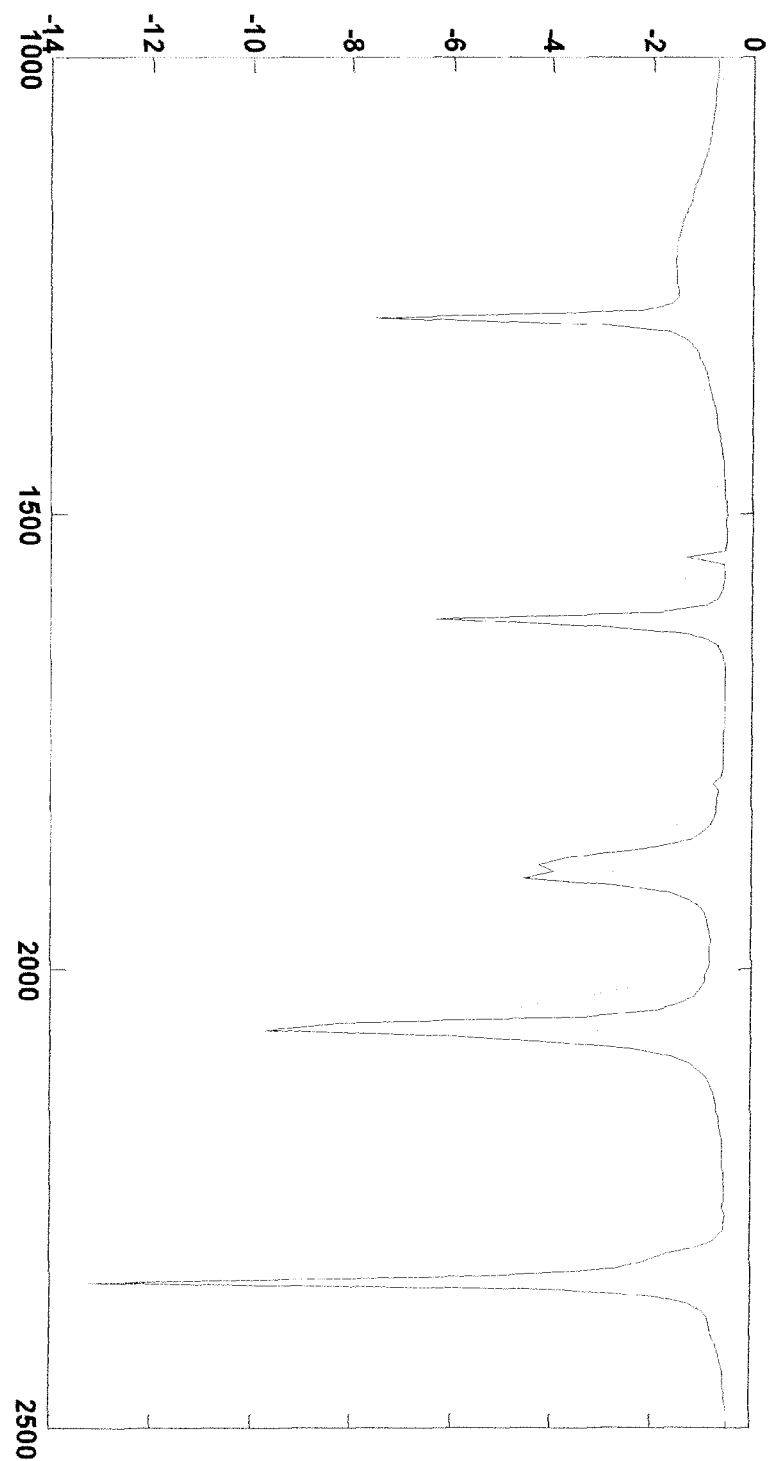
FIG. 3 shows the value of the reflection factor $S_{11}$ of the resonator at different temperatures in the fully reduced state.

For the following tests, the catalytic converter temperature was varied while a gas flow remained consistent. In the test whose result is shown in FIG. 2, a three-way catalytic converter was heated to different temperatures externally by means of a heating sleeve. The test was carried out with a constant gas flow with an air number of approximately 1.48 with a gas composition of 6% $O_2$, 10% $CO_2$ and 5% $H_2O$ in $N_2$. This lean gas mixture leads to oxygen loading of the catalytic converter, and therefore to a very low electrical conductivity of the catalytic converter material (electrically insulating). In the test whose result is shown in FIG. 3, a three-way catalytic converter was heated as described above to different temperatures, wherein a constant gas flow with air number $\lambda \approx 0.96$, with 1.5% CO, 1500 ppm $C_3H_8$, 10% $CO_2$ and 5% $H_2O$ in $N_2$ was conducted through. As a result of the rich gas mixture, the oxygen storage component in the catalytic converter is reduced, that is to say the catalytic converter is emptied and the electrical conductivity of the catalytic converter material rises.

It is readily apparent from FIG. 2 or FIG. 3 that the feature "Resonance frequency of $S_{11}$" (for example first minimum in the frequency spectrum at approximately 1.25 GHz) is highly dependent on the temperature, specifically both in lean conditions (FIG. 2) and also in rich conditions (FIG. 3). At the same time, it is readily apparent from the comparison of FIG. 2 or FIG. 3 that the feature of resonance frequency also shifts with the oxygen loading. At the same time, the resonance frequency also shifts with the geometry, that is to say relatively small deviations in the dimensions cause a shift in the resonance frequency of a wave guide system, as is known for example from "R. F. Harrington, Time-Harmonic Electromagnetic Fields, The IEEE Press Series on Electromagnetic Wave Theory, Wiley Verlag (2001), pages 317-321". The geometry itself is also dependent on the temperature owing to the coefficient of thermal expansion of the catalytic converter housing and of the catalytic converter monolith.

Figure 4:
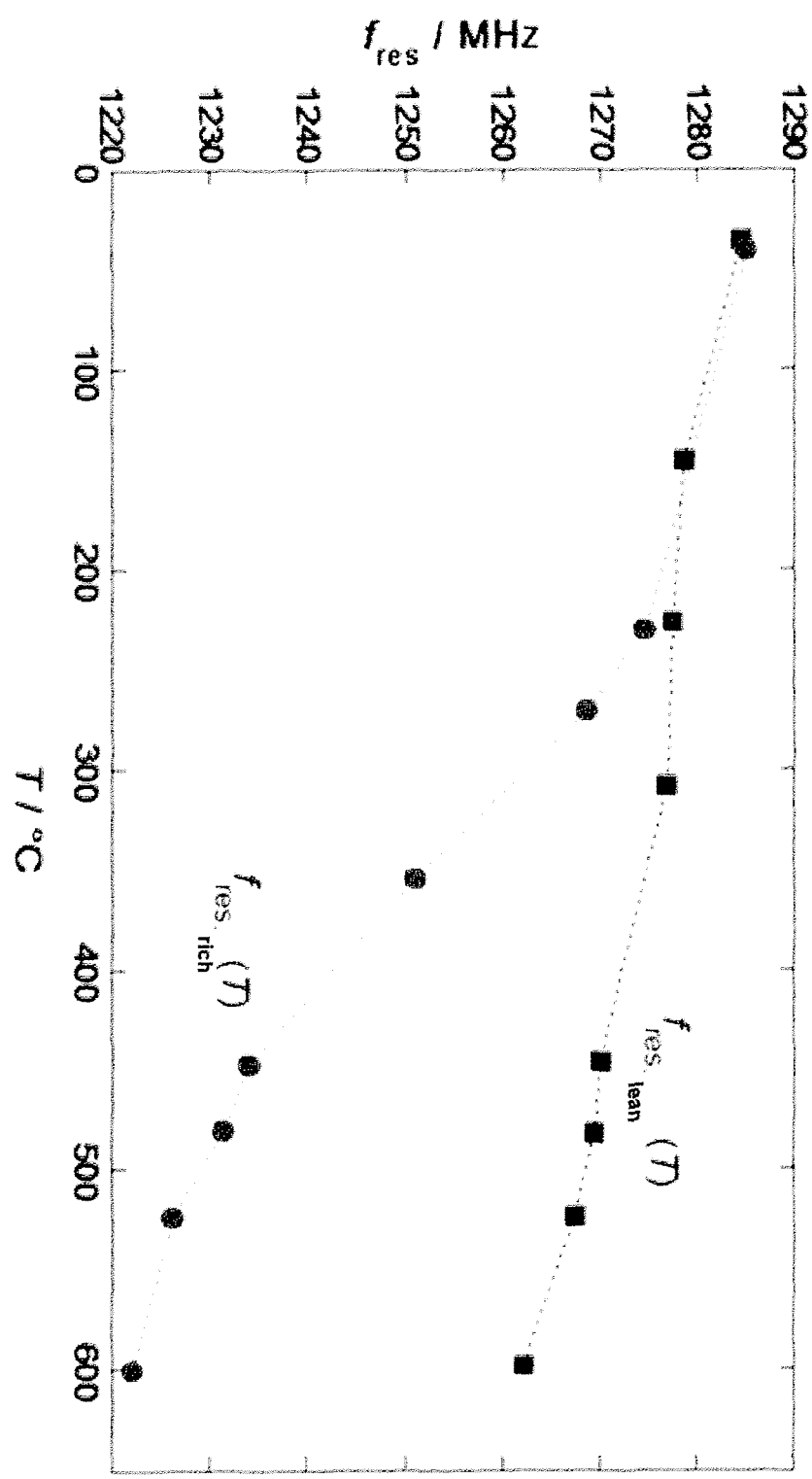
FIG. 4 shows the resonance frequency versus the temperature, in each case in the fully oxygen-laden state and with the catalytic converter fully reduced.

With the aid of the behaviour, hitherto not understood, in FIG. 4, there is now the expedient possibility of a calibration in the vehicle. The measured first resonance frequency in lean conditions and in rich conditions (between approximately 1200 and 1300 MHz depending on the temperature) is plotted, in each case as a function of the temperature, in FIG. 4. It is clear here that the curves overlap at low temperature, whereas the curves diverge only at high temperature. In particular, the points are congruent at room temperature.

By means of these measurement results, a calibration can now be carried out. This will be explained here by way of example for the case of the resonance frequencies as a signal feature.

Firstly, the resonance frequency $f_{res,measured}(T_0)$ is measured at a known temperature $T_0$ which lies below the temperature at which the curves start to diverge. $T_0$ may be for example the ambient temperature when the vehicle is at a standstill. The resonance frequency $f_{res,measured}(T_0)$ will lie exactly on the curve in FIG. 4 only in rare cases. Said resonance frequency however defines a basic state. In FIG. 4 it is possible to see, for a certain geometry, the general temperature dependency of the resonance frequency in the lean state (that is to say the profile of the resonance in the "oxygen-laden" state) $f_{res,lean}(T)$ and in the rich state $f_{res,rich}(T)$ (resonance of the state without oxygen loading). The resonance frequency $f_{res,measured}(T_0)$ measured at $T_0$ can now be set in relation to the resonance frequency in lean conditions at $T_0$, that is to say to $f_{res,lean}(T_0)$. For example, a corrective factor $K_1$ may be defined as follows:

$$f_{res,measured}(T_0)=K_1 \times f_{res,lean}(T_0) \tag{1}$$

By means of said corrective factor, the profile of the basic state $f_{res,full}(T)$ in the fully oxygen-filled case can then be defined as follows:

$$f_{res,full}(T)=K_1 \times f_{res,lean}(T) \tag{2}$$

The same applies for $f_{res,empty}(T)$. For increased accuracy, such a factor $K_1$ may however also be temperature-dependent ($K_1(T)$). As an alternative to the corrective factor, a resonance frequency difference may also be taken into consideration for the calibration:

$$f_{res,measured}(T_0)=\Delta f_{res}+f_{res,lean}(T_0) \tag{3}$$

The profile of the basic state $f_{res,full}(T)$ in the fully oxygen-filled state would then be calculated in accordance with equation (4):

$$f_{res,full}(T)=\Delta f_{res}+f_{res,lean}(T) \tag{4}$$

This applies correspondingly for $f_{res,empty}(T)$. The oxygen-filled basic state (100% oxygen loading, electrically insulating) is thus defined. Based on the establishment from FIG. 4 that there is a profile for the behaviour in the emptied state ($f_{res,rich}(T)$), a calibration for the oxygen-depleted case can be defined analogously to that described above.

The state of the catalytic converter component can thus be traced back to the curve in FIG. 4, which can then serve for example as a basis for the analysis and regulation of the exhaust-gas aftertreatment system. The curve in FIG. 4 may be of different appearance in terms of the absolute values for different engine types. With the concept according to the invention, it is nevertheless possible in any case for the behaviour to be transferred to a curve as in FIG. 4.

The method becomes even more precise if a point, which arises in any case during driving operation, at which the catalytic converter is either definedly laden with oxygen or definedly reduced occurs and said point is likewise taken into consideration as a node. At a known temperature $T_n$, the lean curves $f_{res,lean}(T_n)$ or the curves in the emptied state $f_{res,rich}(T_n)$ can then be adapted. An example for an oxygen-laden operating state may be an operating phase of suitable duration after an overrun fuel cut-off. An emptied state may analogously arise after an enrichment phase of suitable type and duration. From this it is possible to derive a function for the on-board diagnosis, because a comparison with the new state of the catalytic converter yields a representation of the aging over the service life. As already explained in the introduction, the oxygen storage capacity is coupled to the state of the catalytic converter, such that a high storage capacity indicates a catalytic converter which is still functioning well.

It is important to point out here that a signal feature may be not only the resonance frequency of the reflection factor $S_{11}$ but rather also other variables derived therefrom such as for example the damping in the case of resonance, the damping at a certain frequency or the width of a resonance point. Equations (1) to (4) must then be correspondingly adapted.

Other parameters which describe the high-frequency characteristics may also be used. Examples here are the further S parameters or else combinations of S parameters or combinations of features extracted from a plurality of S parameters. Mentioned here as an example are the losses. In this case, too, equations (1) to (4) must then be correspondingly adapted.

It is additionally pointed out here that, according to the invention, in principle all resonance points are suitable for a correction as described above. Furthermore, different features measured at different resonance points (in different frequency ranges) may also be combined.

In the method according to the invention, reproducible conditions are important. The fact that the mentioned installation of reflection grates may be advantageous here has already been shown in the above-cited document DE102008012050. In both cases, the magnitude of the forward transfer function $S_{21}$ of the resonator was measured, once without the reflection grate and once with the reflection grate. The sequence of maxima and minima of the measurement with reflection grates is clearer and less erratic. Owing to the shielding action of the reflection grate, the field no longer penetrates, or penetrates to a lesser extent, into the region of the connection pipes. The result is a resonator which, from a high frequency aspect, is more clearly defined and independent of the form of the connection pipes. This may be advantageous because the conical transitions between the catalytic converter housing and the connection pipes, in particular at the gas inlet, are designed according to flow aspects, for example such that the ceramic honeycomb body is flushed through uniformly by the gas.

Operation without the reflection grate is possible but may under some circumstances lead to increased outlay for the inversion of the relationship between the catalytic converter state and the measured S parameters.

This calibration process according to the invention of the high-frequency measurement system is also expedient for the detection of the loading of other catalytic converter types which store gases or soot particles, such as for example $NO_x$ storage catalytic converters, SCR catalytic converters or diesel particle filters, if, at sufficiently low temperatures, a distinction can no longer be made between the laden and unladen states.

The invention claimed is:

1. A process for calibrating a measurement device for measuring electrical properties of a component for exhaust-gas aftertreatment, which component stores exhaust-gas constituents and is arranged in a housing in an exhaust-gas aftertreatment system of a vehicle, comprising
measuring the electrical properties of the component by the application of microwaves which are coupled in and/or coupled out by at least one antenna arranged in the housing at the inflow side and/or at the outflow side,
designating a measured electrical property of the component which is measured while a temperature of the component is a low temperature as a calibration benchmark of the measurement device, and
correcting the measurement device by applying the calibration benchmark as a corrective value to measurements taken by the measurement device,
wherein, the low temperature at which measurement of the calibration benchmark is made is a temperature at which a distinction cannot be made between different storage states of the component.

2. The process according to claim 1, wherein,
measurement of the electrical properties of the component and calibration of the measurement device comprises use of resonance frequency.

3. The process according to claim 1, wherein,
the measurement device is configured to measure electrical properties of a three-way catalytic converter as the component.

4. The process according to claim 1, further comprising
determining a calibration measurement based on a temperature dependency of a measured electrical property of the component, and
adjusting measured values of electrical properties of the component over the service life of the component on the basis of the calibration measurement.

5. A process for assessing the aging of a component in an exhaust-gas aftertreatment system, comprising
calibrating a measurement device in accord with claim 1,
measuring, with the calibrated measurement device, electrical properties of the component, said measuring including measurements of the component in a laden state and measurements of the component in an unladen state,
calculating a difference in measured electrical properties of the component, between the electrical properties of the component measured in the laden state and the electrical properties of the component measured in the unladen state, and
determining, based on the calculated difference in measured electrical properties of the component, an overall storage capacity of the component in an aged state in relation to an overall storage capacity of the component in a new state.

6. The process according to claim 1, wherein,
the component and the antennae at the inflow side and/or at the outflow side are surrounded by a microwave reflector for delimiting a resonator volume of the housing.

7. A process for controlling an engine, comprising
calibrating a measurement device in accord with claim 1,
measuring, with the calibrated measurement device, electrical properties of the component,
determining a storage state of the component based on the measured electrical properties of the component, and
regulating an engine control based on the determined storage state of the component.

8. The process according to claim 1, wherein,
measurement of the electrical properties of the component and calibration of the measurement device comprises use of amplitude.

9. The process according to claim 1, wherein,
measurement of the electrical properties of the component and calibration of the measurement device comprises use of a quality of the housing.

10. The process according to claim 1, wherein,
measurement of the electrical properties of the component and calibration of the measurement device comprises use of multiple frequency ranges.

11. The process according to claim 1, wherein,
the measurement device is configured to measure electrical properties of an $NO_x$ storage catalytic converter as the component.

12. The process according to claim 1, wherein,
the measurement device is configured to measure electrical properties of an SCR catalytic converter as the component.

13. The process according to claim 1, wherein,
the measurement device is configured to measure electrical properties of a diesel particle filter as the component.

14. A process for calibrating a measurement device for measuring electrical properties of a component for exhaust-gas aftertreatment, which component stores exhaust-gas constituents and is arranged in an exhaust-gas aftertreatment system of a vehicle, comprising measuring, as a base measurement, the electrical properties of the component by the application of microwaves, the base measurement being made in a preliminary operation of the component, prior to any aging of the component, and while the component is at a temperature below a predetermined threshold temperature, measuring, as a normal operation measurement, the electrical properties of the component by the application of microwaves, the normal operation measurement being made during normal operation of the component, and while the component is at a temperature below the predetermined threshold temperature, determining a difference between the electrical properties measured in the normal operation measurement and the electrical properties measured in the base measurement, and designating the determined difference as a corrective value, measuring, as a normal driving measurement, the electrical properties of the component by the application of microwaves, the normal driving measurement being made during normal driving operation of the component, and while the component is at a temperature above the predetermined threshold temperature, and calibrating the measurement device by correcting the electrical properties measured in the normal driving measurement by application of the corrective value, wherein, the predetermined threshold temperature is a temperature at or below which measured electrical properties of the component in a laden state and measured electrical properties of the component in an unladen state differ by 10% or less.

* * * * *